(12) United States Patent
Luchinger (10) Patent No.: US 6,804,985 B2
(45) Date of Patent: Oct. 19, 2004

(54) CALIBRATION APPARATUS FOR MULTI-CHANNEL PIPETTES, INCLUDING A TRANSPORT DEVICE FOR RECEPTACLES

(75) Inventor: Paul Luchinger, Uster (CH)

(73) Assignee: Mettler-Toledo GmbH, Greifensee (CH)

(*) Notice: Subject to any disclaimer, the term of this patent is extended or adjusted under 35 U.S.C. 154(b) by 182 days.

(21) Appl. No.: 10/041,565

(22) Filed: Jan. 10, 2002

(65) Prior Publication Data

US 2002/0124627 A1 Sep. 12, 2002

(30) Foreign Application Priority Data

Jan. 10, 2001 (DE) .......................... 101 00 984

(51) Int. Cl.[7] .............................................. G01F 25/00
(52) U.S. Cl. ............................ 73/1.74; 177/52; 141/83; 141/130
(58) Field of Search .................. 73/864.17–864.18, 73/1.74, 863.32; 177/52, 50, 245; 141/83, 94, 99, 129–130; 422/925

(56) References Cited

U.S. PATENT DOCUMENTS

| | | | | |
|---|---|---|---|---|
| 4,824,642 A | * | 4/1989 | Lyman et al. | 73/864.18 X |
| 5,061,639 A | * | 10/1991 | Lung et al. | 73/1.74 X |
| 5,405,059 A | * | 4/1995 | Wadell | 141/83 X |
| 6,231,813 B1 | * | 5/2001 | Ally et al. | 422/100 |
| 6,455,787 B1 | * | 9/2002 | Ingenhoven | 73/1.74 X |
| 6,615,638 B1 | * | 9/2003 | Lochner et al. | 73/1.74 X |

FOREIGN PATENT DOCUMENTS

| | | | | |
|---|---|---|---|---|
| DE | 29917940 U1 | | 1/2000 | |
| WO | WO 92/02787 | * | 2/1992 | 141/94 |

* cited by examiner

Primary Examiner—Thomas P. Noland
(74) Attorney, Agent, or Firm—Burns, Doane, Swecker & Mathis, L.L.P.

(57) ABSTRACT

An apparatus for the gravimetric calibration of multi-channel pipettes contains a balance that has a load receiver configured to support receptacles containing a substance to be weighed. The apparatus has a holder device to support a certain number of the receptacles into which a test liquid is dispensed from the multi-channel pipette. The apparatus further has a transport device for advancing the holder device towards the load receiver. The receptacles are seated in the holder device at equally spaced positions and are one by one delivered to and subsequently removed from the measuring device.

26 Claims, 10 Drawing Sheets

CALIBRATION APPARATUS FOR MULTI-CHANNEL PIPETTES, INCLUDING A TRANSPORT DEVICE FOR RECEPTACLES

This application claims priority under 35 U.S.C. §§ 119 and/or 365 to 10100984.4 filed in Germany on Jan. 10, 2001; the entire content of which is hereby incorporated by reference.

BACKGROUND

1. Field Of The Invention

The invention relates to an apparatus to calibrate multi-channel pipettes by means of a measuring device, and it also relates to a device for transporting receptacles containing a test liquid to a measuring device.

2. Background Information

Pipettes are instruments for transferring defined amounts of liquids from one container to another and are used in particular in laboratories. The dispensing of liquids by means of pipettes is often the first step in a series of analytical experiments. Multi-channel pipettes are particularly efficient to work with, because they allow liquid to be aspirated simultaneously from one or more containers and to be dispensed into several receptacles at once. It is of particular importance that the volume of liquid taken in and dispensed to other containers is the same in all channels. In view of the strict requirements on the accuracy of the transferred volume, pipettes used for the foregoing purpose, especially multi-channel pipettes, have to be tested several times in the course of a year. In addition, verification tests of pipettes are required under official guidelines and international standards. A verification test is often referred to as a calibration.

For example, piston pipettes with an air cushion, in volume sizes above one microliter, can be calibrated by a gravimetric method, normally using distilled water as test liquid and calculating the volume from the weight and density of the water held by the pipette. Environmental factors including temperature, barometric pressure and relative humidity of the air are taken into account in the volume calculation. The specifics of the gravimetric test method are described, e.g., in the draft standards pr-EN 8655 or ISO/DIS 8655, part 6. In variable-volume pipettes, the test is performed at 100%, 50%, and at a smaller volume of at least 10% of the nominal capacity. For a complete calibration test according to the standard, a series of at least ten consecutive measurements has to be performed at each of the tested volumes. To test a multi-channel pipette, pr-EN 8566 or ISO/DIS 8655, part 6, section 7.3, requires that all channels must be filled with the test liquid, but only the liquid in the channel that is currently being tested is dispensed into the recipient container (also referred to as receptacle) on the load receiver of a weighing device. In other words, each channel has to be measured individually. In a more extensive procedure which is also described in the aforementioned standards and requires 30 measurements in a single-channel pipette, the calibration test of a multi-channel pipette with, e.g., 12 channels requires 360 cycles of aspirating, dispensing and weighing, so that the test can take several hours, especially if more than one volume is to be tested in a multi-channel, variable-volume pipette.

A gravimetric test apparatus for multi-channel pipettes is described in the German utility model DE U1 299 17 940, in which a separate receiving device is provided for each pipette channel (with a minimum of two), and a separate weighing cell is provided for each receiving device. In other words, the apparatus has a separate weighing cell for each pipette channel. For a 12-channel pipette, this concept would require 12 weighing cells.

The foregoing arrangement for a gravimetric test apparatus for multi-channel pipettes has the disadvantage that it requires more than one weighing cell, i.e., as many weighing cells as there are pipette channels, where each of the weighing cells would also have to be calibrated. Thus, the concept is very expensive to put into practice. As a further disadvantage, the weighing cells have to be arranged relatively close to each other. This limits the level of accuracy that can be achieved, because for the weighing cells to be compact enough, they would have to be strain-gauge load cells, which will not in all cases have the accuracy required for the calibration of pipettes. It is furthermore hard to avoid that the heat build-up and heat flow in a close aggregation of weighing cells can cause temperature gradients that are detrimental to the weighing accuracy. The foregoing concept of multiple weighing cells could be realized with electromagnetic compensation cells, but the latter would have to be arranged farther apart from each other than would be compatible with the distance of the receptacles when they are filled by dispensing the liquid from the channels of the pipette. Thus, the receptacles would have to be moved to the respective load receivers, which would require a complex system of rods and levers. The higher accuracy available with multiple electromagnetic compensation cells thus comes at a high cost due to the complexity of monitoring and calibrating the multiple weighing cells.

SUMMARY OF THE INVENTION

The present invention therefore has the objective of providing an apparatus for the gravimetric calibration of multi-channel pipettes with a transport device that advances the receptacles to the measuring device. The apparatus should have an uncomplicated design that causes no loss of precision of the calibration measurements, can be realized at a favorable cost, and has a faster operating speed, so that a multi-channel pipette can be calibrated in a reasonable amount of time.

An apparatus for the gravimetric calibration of multi-channel pipettes according to the present invention contains a balance that has a load receiver configured to support receptacles containing a substance to be weighed. The apparatus has a holder device to support a certain number of the receptacles into which a test liquid is dispensed from the multi-channel pipette. The apparatus further has a transport device for advancing the holder device towards the load receiver. The receptacles are seated in the holder device at equally spaced positions with a defined distance from each other. The transport device has means whereby one after another of the receptacles can be delivered to and subsequently removed from the measuring device.

Because the apparatus according to the invention contains only one balance, it represents a more cost-effective solution. Due to its uncomplicated design, the apparatus also takes up less space than known state-of-the-art arrangements. With the need for only one balance, it is possible to use a high-precision balance that is equipped with one of the known self-calibration mechanisms and meets the stringent requirements described in the standards for calibrating multi-channel pipettes. The transport device and/or the holder device are designed to precisely position the receptacles on the load receiver. The apparatus according to the invention can be offered either as an accessory to a high-precision analytical balance of a standard model version, or it can also be offered as an integrated system.

In a preferred embodiment of the invention, the transport device is encased in a housing, with the balance also installed in the same housing. The load receiver is arranged on top of the balance and extends upwards into the holder device through an opening of the housing. The load receiver has two lateral wing portions with indentations at their upper ends for the positive positioning of the suspended receptacle.

In an advantageous embodiment of the invention, the defined distance between the receptacles in the holder device corresponds to the spacing of the tips of a multi-channel pipette that is to be calibrated, and the number of the receptacles in the holder device is not less than the number of pipette tips.

The transport device for advancing the holder device to the load receiver can be used for applications other than the calibration of multi-channel pipettes. The capability to transport receptacles in a holder device to a measuring device would also be useful, e.g., with a spectrometer.

The transport device is equipped with a holder device for receptacles that can be filled with a liquid or a pourable solid substance. The arrangement of the receptacles in the holder device is such that they center themselves and can be individually handled. The holder device is designed to be moved in the transport device and has means for damping the movement of the receptacles if an external influence displaces them from their rest positions. The transport device is equipped to deliver the receptacles one by one to the measuring device. In the same movement as one receptacle is removed from the measuring device, a next following receptacle is delivered to the measuring device.

The receptacles can have a round, oval or rectangular cross-section. When seated in the holder device, they are equally spaced at a defined distance from each other. At its top end, each receptacle has a pair of rigid horizontal suspension members by which the receptacles are suspended in indentations of a holder rack in the holder device.

In a preferred embodiment, the suspension members consist of rod members attached to the receptacles by sockets that partially embrace the circumference of the receptacle. The rod members have inward-pointing cones at their far ends, and at least one of each pair has a double cone, i.e., two cones joined at their bases and pointing away from each other. A ring groove is formed where the tip of the inward-pointing cone meets the outward-pointing tip of the double cone. The ring groove serves to define the seating position of the suspension member in the indentation of the holder rack.

In a particularly advantageous embodiment of the invention, the holder device is designed so that it can be separated from the transport device.

The holder device has a cover to avoid contamination and reduce evaporation of the liquid in the receptacles. In addition, the holder device has at least one tub located near the fill openings of the receptacles. The tubs can be filled with the test liquid which, by evaporating and saturating the atmosphere inside the holder device, will further contribute to reducing the evaporation of the test liquid from the receptacles. The underside of the holder device is designed to keep out air circulation when the holder device is set down on a flat surface, and particularly to prevent air drafts from reaching the load receiver of the analytical balance when the apparatus is used for pipette calibration.

In a further developed advantageous embodiment, the transport device is designed to perform a combined movement where the holder device is moved horizontally forward or backward while being simultaneously raised and lowered. The drive mechanism for the combined movement works with a single motor that is provided in the transport device.

An advantageous embodiment of the invention provides for a transport carriage that moves in a transport channel of the transport device and has a seat to receive the holder device. The movement of the transport carriage in the transport device is guided by at least one transport rack that is part of the transport device. Also, the transport device is preferably equipped with a position sensor to detect the actual position of the holder device or of the transport carriage within the transport device.

In a preferred embodiment, the transport device is encased in a housing, and the drive mechanism is attached to the housing. The drive mechanism has a drive wheel with at least two bolts or rollers. A drive rack with arcuate cutouts is attached to either the transport carriage or the holder device. The bolts or rollers of the drive wheel engage the cutouts of the drive rack so that, when the drive wheel turns, the holder device is moved along the transport channel. The drive rack, the transport rack, as well as the holder rack of the holder device are shaped with the same periodic pitch.

The holder device can be guided by the transport device on a linear or circular path. In the latter case, the holder device could also be of a circular design in the manner of a carousel holder.

In a further developed embodiment of the invention, the receptacles are marked with a code, e.g., at the bottom of the receptacle. The transport device is suitably equipped with a sensor head and with a means of transmitting the coded information from the receptacle bottom to the sensor head. In addition, or as an alternative, the holder device can be marked with a code which can be read by a sensor device that is mounted on the transport device at the same level as the code marking on the holder device.

Further details of the design and function of the inventive apparatus for the gravimetric calibration of multi-channel pipettes and of the transport device for transporting receptacles to a measuring device may be learned from the following description of a preferred embodiment that is represented schematically in the drawings.

DETAILED DESCRIPTION OF PREFERRED EMBODIMENTS

Figure 1:
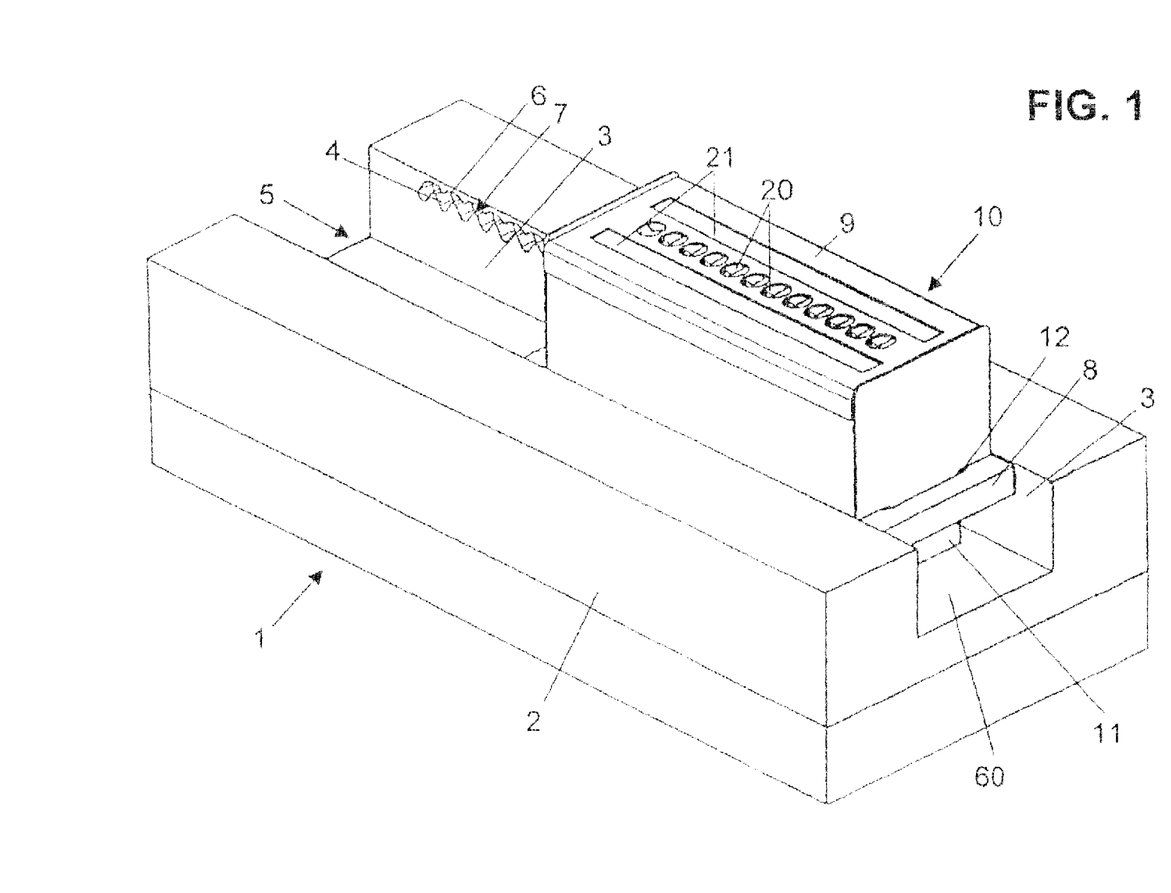
FIG. 1 represents an overall view of an exemplary transport device according to the invention.

An apparatus for the gravimetric calibration of multi-channel pipettes includes an electronic balance with a load receiver, a holder device, and a transport device for receptacles. FIG. 1 illustrates a transport device 1 with a housing 2, and a transport channel 5 running along the center of the housing 2. Transport racks 7 run near the top of the inward-facing side walls 3 of the channel 5. The bottom side 4 of each transport rack has a profile resembling a sine wave with truncated wave tops. The sine-wave profile could for example be formed as a machined recess in each side wall 3, in which case the latter would be made of a thicker material. Alternatively, the sine-wave profile could be part of a rail that is set into the side wall 3. The transport rack 7 is delimited at the top by an upper rack profile 6 in the shape of arches, with the highest points of the arches lying opposite the truncated wave tops of the bottom side 4. A transport carriage 8 is movable in the transport channel, guided by the transport racks 7, as will be described in more detail in the context of FIG. 5. A holder device 10, which could also be called a holding frame, has a foot portion 11 that is seated with a snug fit in a seat 12, e.g. a cut-out, of the transport carriage 8. No additional fastener device is needed to keep the holder device 10 positioned on the transport carriage 8. A cover 9 is set over the holder device 10.

Figure 2:
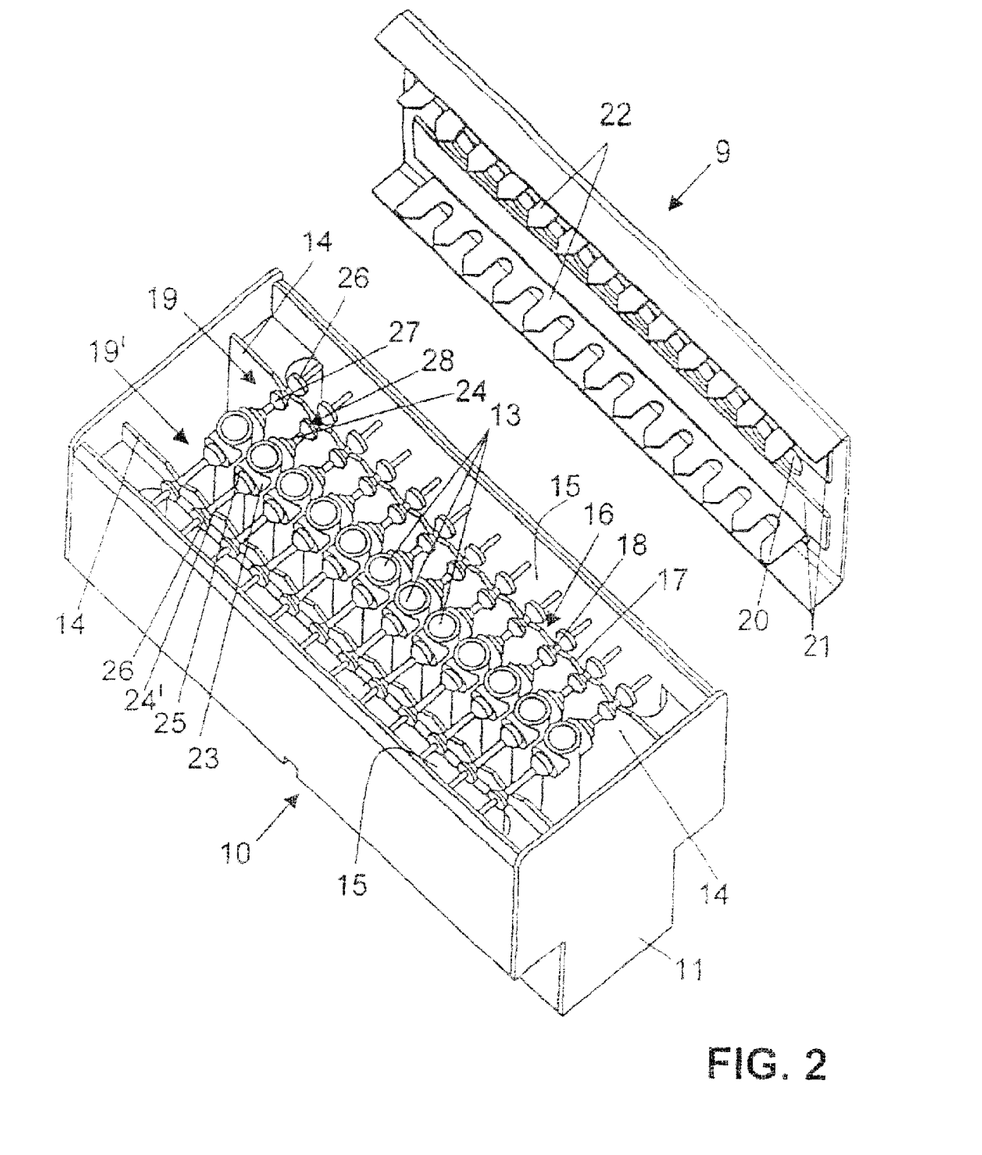
FIG. 2 represents an exemplary embodiment of a holder device for receptacles in a perspective view.
Figures 3A, 3B:
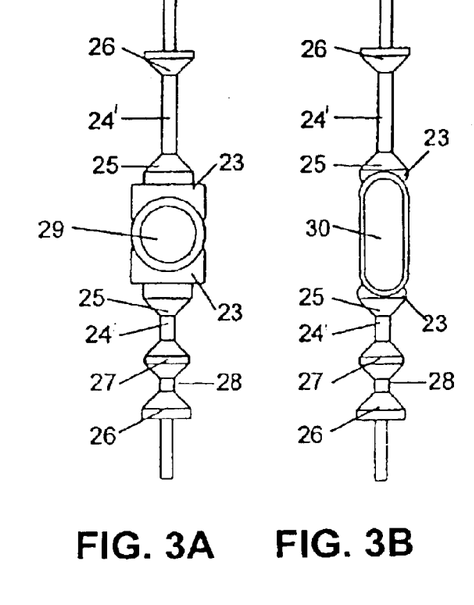
FIG. 3A represents a top view of an exemplary embodiment of a receptacle with its suspension members.
FIG. 3B represents a top view of an exemplary embodiment of a receptacle with its suspension members.
Figure 3C:
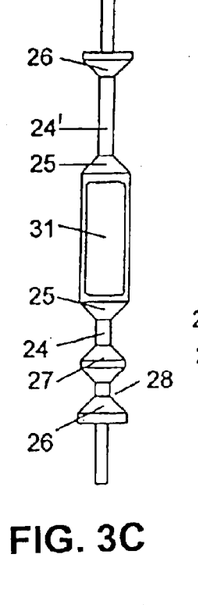
FIG. 3C represents a top view of an exemplary embodiment of a receptacle with its suspension members.
Figure 3D:
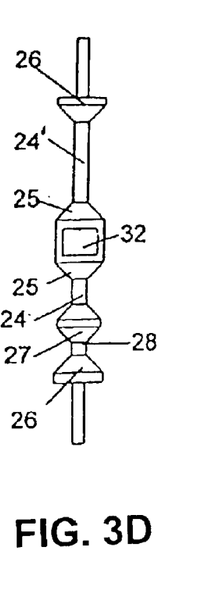
FIG. 3D represents a top view of an exemplary embodiment of a receptacle with its suspension members.

FIG. 2 gives a perspective view, looking from above at an oblique angle at the holder device 10 with the receptacles 13 for the test medium (usually water). In addition, FIG. 2 also shows the cover 9, likewise in perspective, looking at the underside of the cover 9. The holder device 10 includes an oblong T-shaped arrangement of three major parts. The side walls 14 extend from the foot portion 11 almost to the upper edge of the holder device 10. Tubs 15 are arranged on the outside of both side walls 14. The tubs 15 are filled with the same liquid as is used to test the pipettes (normally water), or they contain water-saturated sponges. Their purpose is to saturate the air inside the holder device 10 with humidity to counteract the evaporation of the test liquid in the receptacles 13. A humidity sensor installed close to the tubs 15 may be used to verify the degree of saturation. The side walls 14 have serrated upper rims forming a holder rack 16. The tips 17 and triangular indentations 18 in the rim of one side wall 14 are symmetrically aligned with the tips and indentations of the other side wall 14. The indentations of the holder rack 16 serve as seats for the receptacles 13. The latter are suspended by means of suspension members 19, 19' that are seated in the indentations 18 of the holder rack 16. A series of receptacles 13 are seated in this manner one after the other in adjacent indentations. The holder device 10 is open at the bottom. However, if the holder device 10 is set down on a plane surface, e.g., on the floor 60 of the transport channel (see FIG. 1), the bottom of the holder device 10 is closed off so that no air, and thus no humidity, is exchanged with the ambient atmosphere.

The receptacles 13 are preferably of glass and have an elongated shape with a round cross-section. For example, standardized test tubes are suitable. Polymer containers may also be used in certain cases. The receptacles 13 do not have to be of any specific length, as long as they fit into the holder device 10. Suspension members 19, 19' are attached on opposite sides at the top ends of the receptacles 13 near their fill openings. The suspension members 19 on one side are shaped differently from the suspension members 19' on the opposite side of each receptacle 13. The suspension member 19' has a contoured socket 23 partially embracing the circumference of the receptacle 13. From the socket 23, the guide member 19' continues through an inner cone 25 to a rod member 24', which widens again into an outer cone 26. Close to where the rod member 24' joins the tip of the outer cone 26, the rod member 24' rests in one of the indentations 18 of the holder rack 16.

The suspension member 19 on the opposite side is similar to the suspension member 19' except for an additional double cone 27 between the inner cone 25 and the outer cone 26. One apex of the double cone 27 of the suspension member 19 immediately adjoins the apex of the outer cone 26, so that a ring groove 28 is formed at the juncture of the two apexes. The groove 28 does not need to be a concentric ring groove, as will be explained below in the context of FIG. 4. The ring groove 28 is seated in an indentation 18 of the holder rack 16, providing a positively defined seat for the suspension member 19. The friction between the ring groove and the flanks of the indentation 18 provides a strong damping effect to counteract a tendency of the suspended receptacles 13 to swing back and forth like a pendulum as a result of an outside disturbance. The receptacles 13 are arranged at a minimal distance so that they are not touching each other. Due to the concept of suspending the receptacles 13, they remain parallel to each other and will not touch each other even if the holder device 10 is not in a level position.

The suspension members 19, 19' are preferably made of metal and may be attached to the receptacles 13, e.g., by adhesive bonding. However, it is also conceivable to make the receptacles 13 and suspension members 19, 19' all in one piece, e.g., in a pressure-molding process of a polyester material. Particularly with polyester receptacles, it is beneficial to provide the receptacles with a conductive coating to avoid an accumulation of electrostatic charges.

A receptacle 13 may be dislodged slightly in the transverse direction of the holder device 10, for example as a result of the required wiping of the pipette tips against the receptacle walls. However, the dislodged condition will correct itself after the pipette has been removed from the receptacle wall, as the interaction of the cones with the indentations 18 will cause the suspension members 19, 19' to self-center again in their equilibrium positions.

The transport device 1 in combination with the holder device 10 with the suspension arrangement for the receptacles 13 constitutes an automated transport system in which the receptacles 13 are suspended in self-centering seats and without touching each other. The receptacles 13 can hold a liquid or a pourable substance in the solid phase. In transporting the receptacles 13 to a measuring device, they can be handled, advanced to, and removed from the measuring device one by one. When a receptacle is removed from the measuring device, the next following receptacle is simultaneously advanced into position on the measuring device. The seating of each receptacle 13 with the ring groove 28 resting in the triangular indentation 18 of the holder rack 16 provides a high degree of damping to stop the receptacles from swinging if their equilibrium is disturbed, e.g., by jolting or tilting of the holder device 10. The receptacles 13 furthermore precisely center themselves by means of this seating arrangement, and the arrangement helps to prevent spilling of the substance that is to be measured.

As FIG. 2 further illustrates, the holder device 10 can be closed with a cover 9. The latter may have openings 20 (see FIG. 1) through which the receptacles 13 can be filled and which can have their own closure device. The cover 9 also has transparent windows 21 above the tubs 15, so that an operator can see that the ends of the suspension members 19, 19' are correctly aligned and the tubs are filled with liquid. In addition to preventing the evaporation and contamination of the measuring liquid, the cover 19 also serves to secure the receptacles 13 so that they cannot detach themselves from their seats in the indentations 18 of the holder rack 16, e.g., if the holder device 10 is tilted too far, or if the holder device is moved or set down abruptly by the user. As a securing means, the cover 9 has two retainer racks 22 with prongs which, when the cover 9 is put in place, descend into the spaces between the rod members 24, 24' on the outside of the side walls 14. A more detailed description of how the holder rack 16 and the retainer rack 22 work together will be given in the context of FIG. 8.

FIGS. 3A to 3D show further possible configurations of the receptacles and suspension members as seen from vertically above. The receptacles can have a compact rectangular cross-section (receptacle 32 of FIG. 3D), an oblong rectangular cross-section (receptacle 31 of FIG. 3C), an oval cross-section (receptacle 30 of FIG. 3B), or a round cross-section (receptacle 29 of FIG. 3A). The suspension members 19, 19' are adapted to the size and shape of the respective receptacle in each of the cases 3A to 3D. The now customary spacing of 9 mm between the tips of manual multi-channel pipettes is compatible with a greater variety of designs regarding the cross-sectional shape of the receptacles 13 than the spacing of 4.5 mm, which appears more and more to become the standard for automated multi-channel pipettes. However, even the 4.5 mm spacing can be accommodated with the flexible design possibilities for the receptacles just described. Nevertheless, the suspension members can also have other shapes, not based on rotational symmetry, which recommend themselves in particular if the spacing of the receptacles has to conform to multi-channel pipettes with a small distance between the tips. It is self-evident that the pitch of the indentations (which may also have other than triangular shapes) of the holder rack 16 of the holder device 10 defines the spacing of the receptacles and thus corresponds to the spacing of the tips of a multi-channel pipette that is to be calibrated by means of the inventive arrangement.

Figure 4:
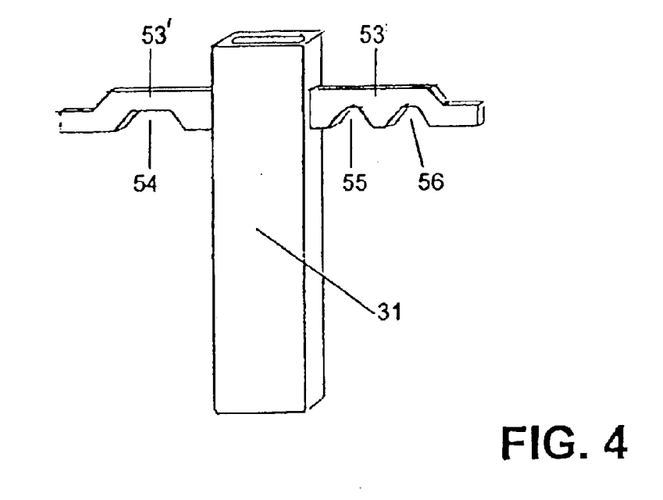
FIG. 4 represents a perspective view of an exemplary alternative design of the suspension members, particularly suitable for narrow receptacles.

FIG. 4 gives a three-dimensional view of a narrow receptacle 31 with an oblong rectangular cross-section. The suspension members 53, 53' are rectangular in cross-section, with a trapeze-shaped indentation 54 on one side and two somewhat narrower indentations or notches 55, 56, also preferably trapeze-shaped, arranged next to each other on the other side. The receptacle 31 is suspended in the holder device 10 at the outer end of the indentation 54 and at the notch 56. The notch 55 as well as the inner end of the indentation 54 serve to set the receptacle 31 in a defined position of a load receiver on a balance, as will be explained in more detail below in the context of FIGS. 6 and 8. The height of the suspension members 53, 53' is reduced at the outer ends. The shape of the suspension members 53, 53', like the previously described shapes and a multitude of other conceivable shapes, provides a stable, self-centering and swing-damping arrangement for the receptacles 31 in a compatibly shaped receiving arrangement of a holder device 10. It is important to match the shape of the serrations on the holder device 10 and the circular notches 28 or notches 56 on the suspension members appropriately so that the suspended receptacles will neither be immobilized by two much friction nor be able to swing back and forth too easily because of too little friction.

Figure 5:
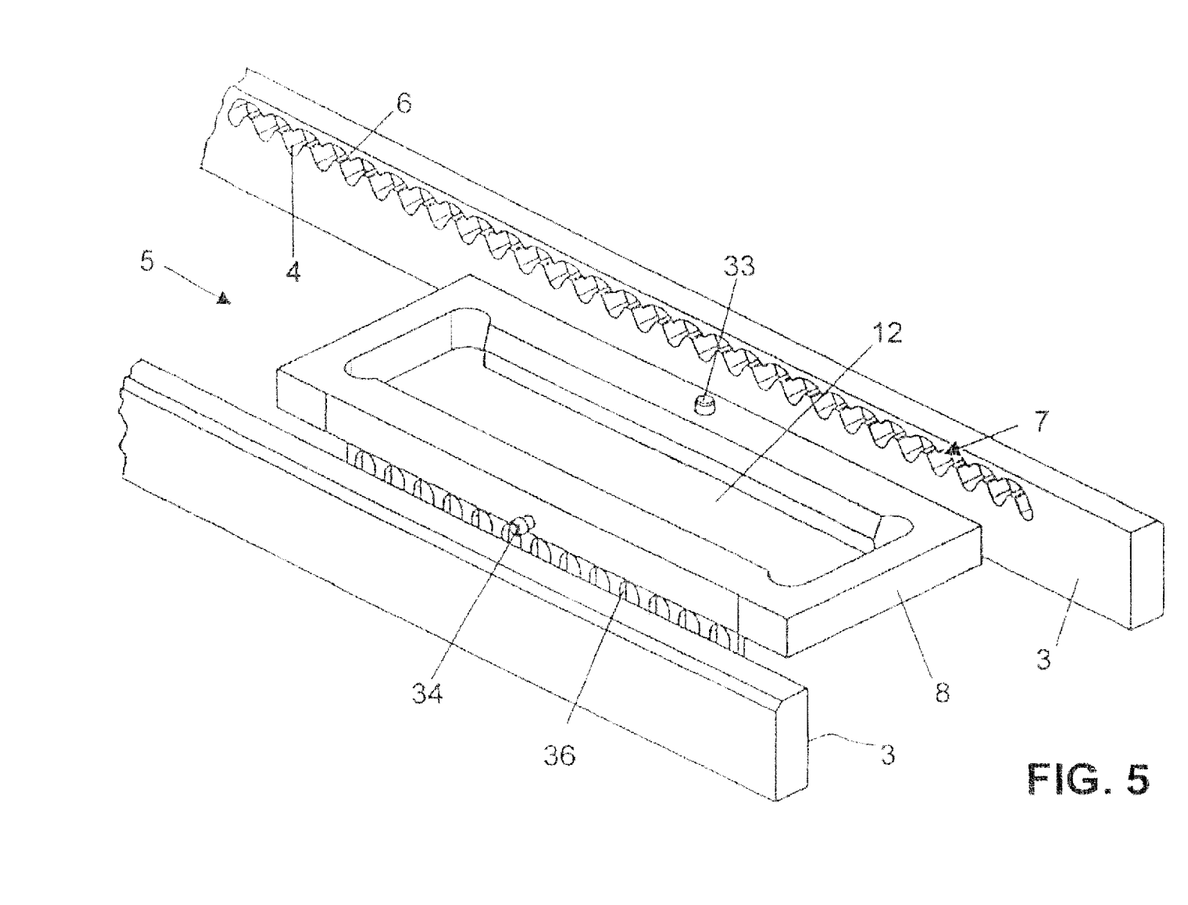
FIG. 5 represents a perspective view of an exemplary transport rack and transport container, shown spatially separated from each other.

FIG. 5 shows the transport carriage 8 in the transport channel 5. For clarity, the channel side walls 3 are shown spatially separated from the transport carriage 8 in the manner of an exploded view. The cutout or seat 12 in combination with the pin 33 is designed to ensure a defined positioning of the holder device 10 in the seat 12 without additional connector means. With at least three laterally projecting guide pegs 34 engaging the transport racks 7, e.g. two guide pegs on one side and one guide peg on the other side, the transport carriage 8 is guided along the transport rack in an up-and-down zigzag motion. The guide pegs 34 are, e.g., attached to axles that turn in roller bearings in the transport carriage 8, with two of the axles arranged at the front and back on one side of the carriage 8 and one axle arranged in the middle of the other side of the carriage 8. The transport carriage 8 cannot leave its track or become jammed in a skewed position, due to the special design of the transport rack 7 where the wave tops of the approximately sine-curved bottom side 4 are centered in the arches of the top side 6.

The transport rack 7 and the holder rack 16 of the holder device 10 have the same pitch, matched to the spacing of the tips of a multi-channel pipette that is to be calibrated with the inventive apparatus.

As a further advantage of the special design of the transport rack 7, the advancement of the transport carriage 8 with the simultaneous up-and-down movement can be driven by a single drive mechanism. One part of the drive mechanism is connected to one of the side walls 3 of the transport channel 5, while another part is connected to the underside of the transport carriage 8. The part connected to the transport carriage 8 is a rack 36 with arcuate cutouts arranged at the same pitch as the transport rack 7 and the holder rack 16, as shown in FIG. 5 on the side of the transport carriage that faces towards the viewer. The transport device 1 advantageously has a positioning sensor (which is not seen here) operable to determine the actual position of the holder device 10 and the transport carriage 8 in relation to the transport device 1.

Figure 6:
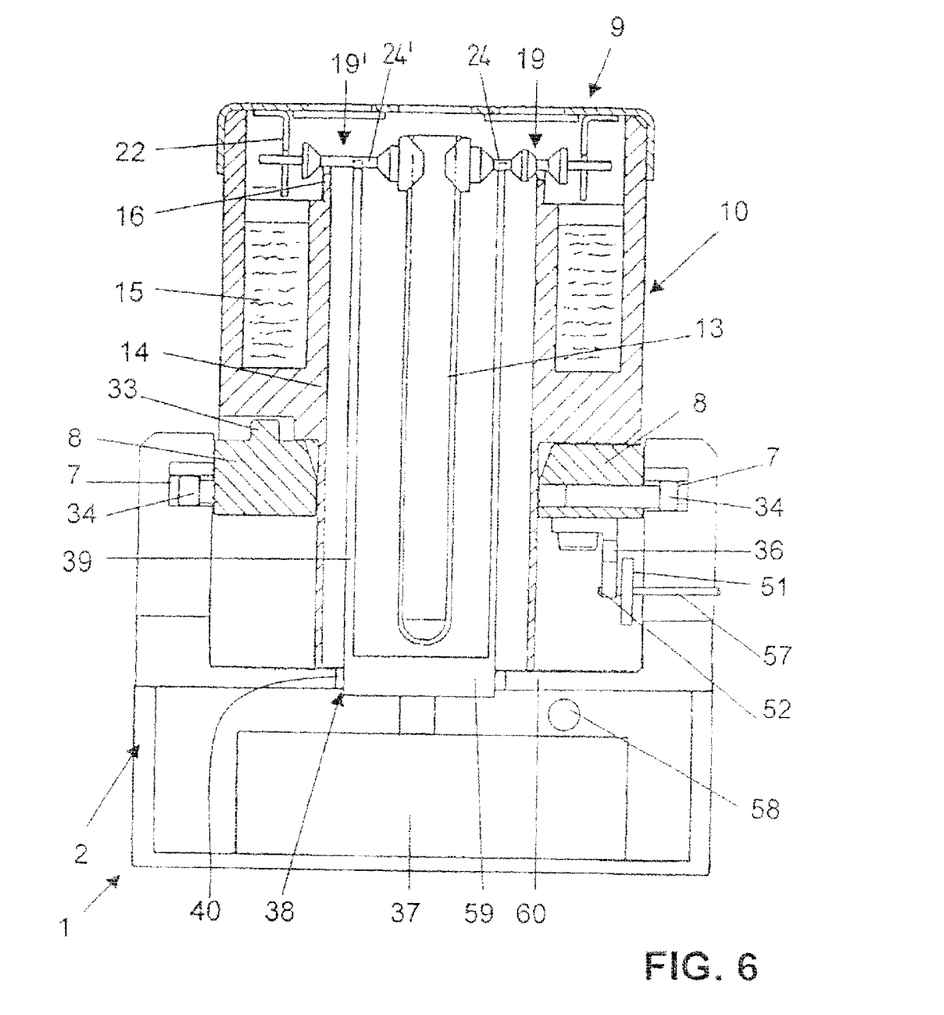
FIG. 6 represents a sectional view of an exemplary embodiment of a load receiver inside the holder device with a receptacle in place.

The transport carriage 8 with the entire holder device 10 including the receptacles 13 is advanced towards a balance 37 which is arranged in the bottom part of the housing 2 at an approximately central location of the transport channel 5. As shown in FIG. 6, a load receiver 38 is mounted in an upright position on the balance 37. The load receiver 38 passes through an opening 40 in the floor 60 of the transport channel 5. The load receiver 38 has a base 59 with vertically extending wings 39. A receptacle 13 is shown seated on the wings 39 at points closer to the receptacle than the serrated rims of the holder rack 16. When the apparatus is in operation, the holder device 10 is closed by the cover 9, and the two lateral tubs 15 are filled with water. FIG. 6 further illustrates how the guide pegs 34 of the transport carriage engage the transport racks 7 on both sides of the transport channel 5. The drive rack 36 is shown on the right mounted to the underside of the transport carriage 8. An eccentric bolt or roller 52 on a drive wheel 51 is shown engaging the drive rack 36. The drive wheel 51 is rotationally coupled to a gear (not shown) that is mounted on the same shaft 57 as the wheel 51. The gear meshes with a worm gear (likewise not shown) which, in turn, is driven by a motor (not shown).

The balance is accommodated inside the housing 2 of the transport device 1 and is thereby protected from air drafts. The load receiver 38, being inside the holder device 10 is completely protected from air drafts during the time periods when the transport movement is interrupted for the weighing, i.e., when the holder device 10 is at the lowest point of its path and the side walls 14 are touching the floor 60 of the transport channel 5.

A pressure sensor 58 and/or a temperature sensor can be installed near the balance 37 to monitor the environmental parameters that enter into the determination of the density of the test liquid.

The transport device 1 is driven by a single motor, which is accommodated in the housing 2 of the transport device 1 below and to the side of the transport rack 7. The drive mechanism is designed to guide the transport carriage 8 in a combined movement, advancing horizontally as well as moving up and down at the same time.

Figure 7:
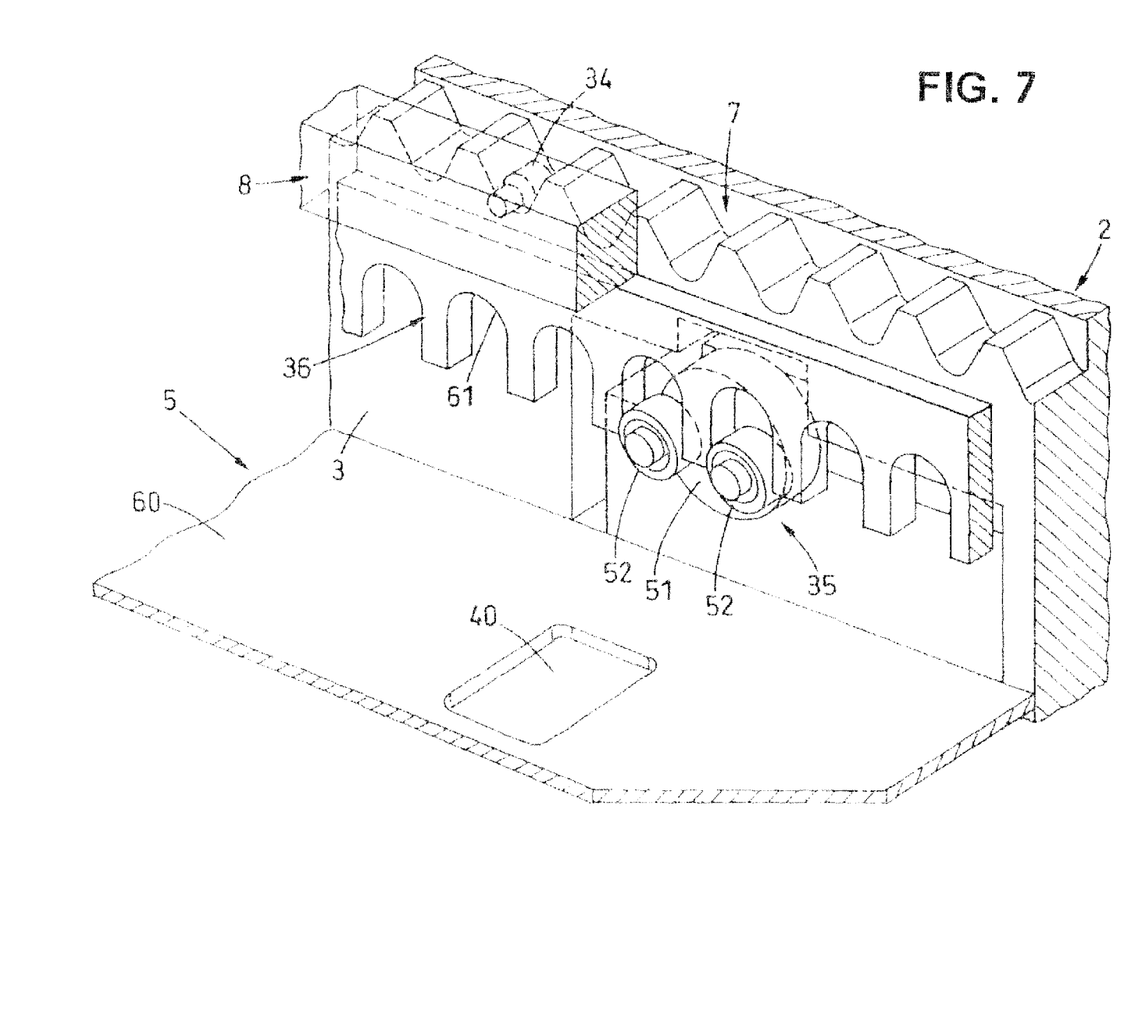
FIG. 7 represents an exemplary embodiment of the drive mechanism at a lowest position of a transport movement.

FIG. 7 represents a perspective view directed from the transport channel 5 towards the drive mechanism 35 as well as the transport rack 7 to illustrate how they work together. Shown in the foreground is the opening 40 for the passage of the load receiver 38 through the floor 60 of the transport channel 5. The drive wheel 51 carries two eccentric bolts or rollers 52 at symmetrically opposite locations from the shaft 57 (see FIG. 6). The eccentric rollers 52 engage the arcuate cutouts of the drive rack 36. The guide peg 34 of the transport carriage 8 rests in one of the concavities of the transport rack 7. The size and distance of the bolts or rollers 52 are such that the latter will precisely engage two consecutive arches 61 of the drive rack 36. At the beginning of a cycle of the carriage movement, the two bolts 52 are positioned horizontally side by side, as shown in FIG. 7, while the transport carriage 8 with the drive rack 36 is at the lowest point of the movement cycle. This is the position in which the weighing takes place. As the drive wheel 51 is subsequently turning, one of the bolts moves downward and leaves the drive rack 36, while the other bolt 52 moves upward and deeper into the arch 61, whereby the transport carriage 8 is advanced horizontally as well as lifted vertically, as the guide pegs 34 follow the contour of the transport rack 7. At the point where one bolt 52 is positioned vertically above the other, the guide peg 34 glides on one of the flattened wave tops of the transport rack 7. This position represents the highest point in the cycle in which the receptacles 13 are one by one set from the holder device 10 onto the load receiver 38 and back onto the holder device 10. This exchange cycle will now be explained in more detail based on FIG. 8.

Figure 8:
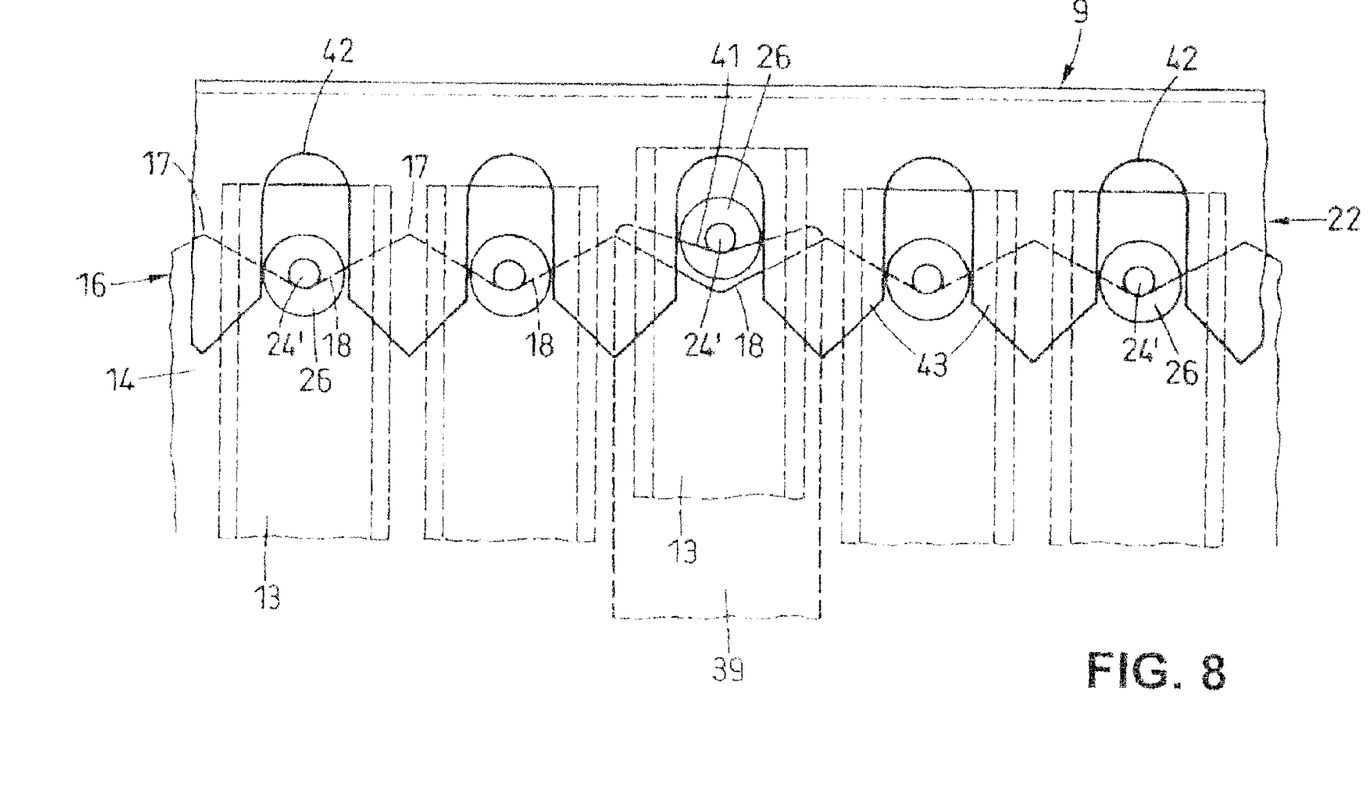
FIG. 8 illustrates in a detail view from the side an exemplary manner by which an exemplary transport device and load receiver work together.

FIG. 8 illustrates in a side view how the transport device 1, the holder device 10 and the load receiver 38 (see FIG. 6) work together. The tops of both wings 39 of the load receiver have V-shaped depressions 41 as seats for the receptacles 13. The drawing further illustrates how the retainer rack 22 of the cover 9 prevents the receptacles 13 from falling out of the seats in the holder device 10.

When the holder device 10 with the transport carriage 8 and the drive rack 36 are at one of the low points of the movement cycle, the wings 39 of the load receiver extend about 2 mm above the triangular depressions 18 of the holder rack 16 on the side walls 14 of the holder device 10. The depressions 41 of the wings 39 are about 1 to 2 mm shallower than the vertical distance between the depressions 18 and the tips 17 of the holder rack 16. With this arrangement, the sequence of movements of putting one after the other of the receptacles 13 on the load receiver 38 is as follows: at the beginning of the cycle, the holder device 10 is pushed upward and forward by the drive mechanism, as described above in the context of FIG. 7. The lifting movement takes the depression 18 of the holder rack 16 to a slightly higher level than the outer corner of the wing 39 of the load receiver 38. In the subsequent downward movement of the holder device 10, the load receiver catches the receptacle by the rod members 24, 24', and the latter glide to the bottoms of the V-shaped depressions 41. At this point, the receptacle 13 is suspended in the load receiver 38, free from contact with any part of the holder device 10, so that the weighing process can now take place. In the same movement as one receptacle 13 is put on the load receiver 38, the holder rack 16 lifts the receptacle before it out of the V-shaped depressions 41 of the load receiver wings 39 during the upward movement of the holder device 10.

The retainer racks 22 secure the receptacles 13 against falling out of the triangular depressions 18 in the holder rack 16, as the borders of the cutouts in the retainer rack 22 overlap the tips 17 of the holder rack 16. This still allows the receptacles 13 to tilt sideways in their seats on the load receiver 38, as the arches 42 between the prongs 43 of the retainer rack 22 are high enough to allow tilting while preventing the receptacles 13 from falling out of their captive positions.

Figure 9:
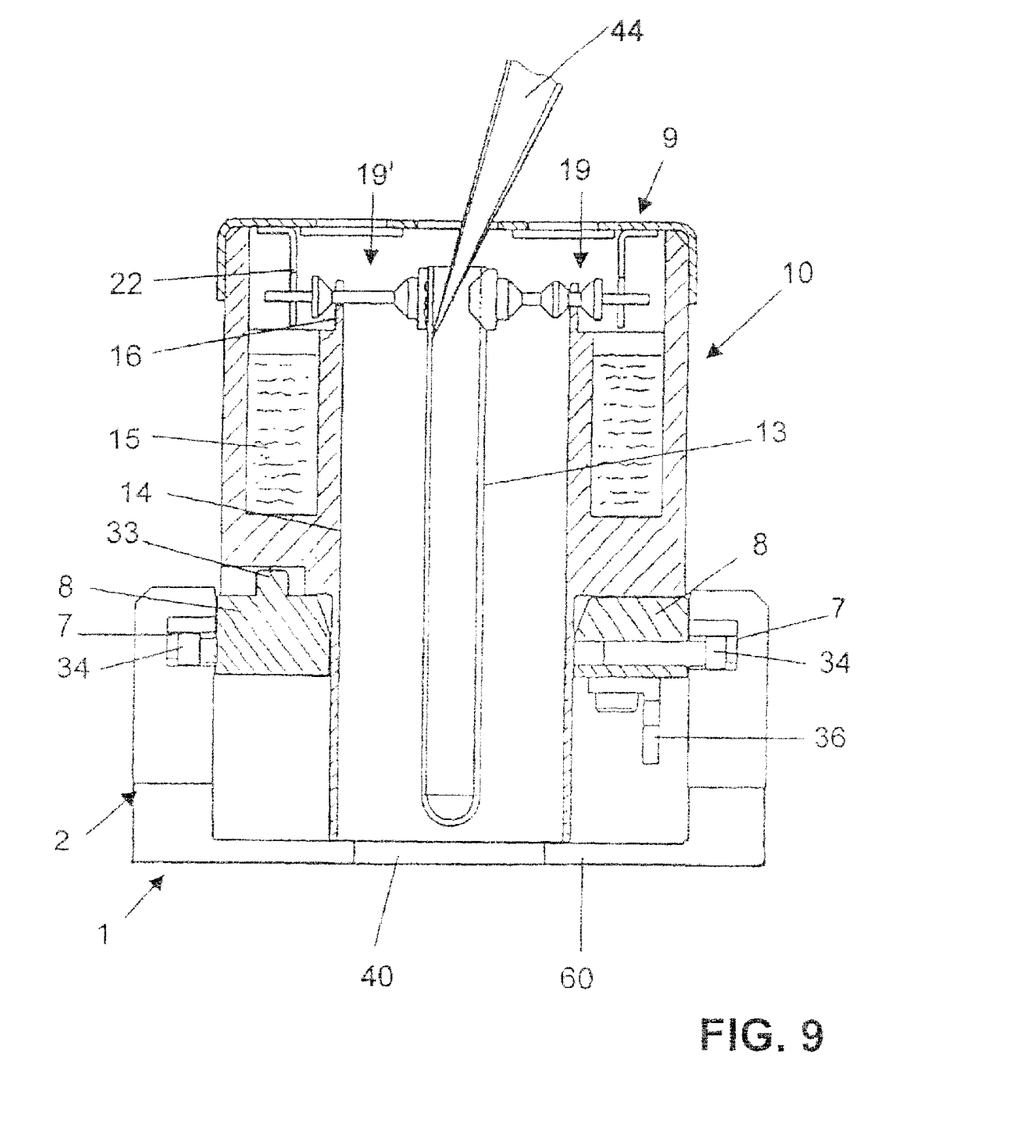
FIG. 9 represents a cross-sectional view of an exemplary holder device.

FIG. 9 represents a transverse cross-section of the holder device 10, illustrating how a liquid is dispensed from a pipette tip 44 into one of the receptacles 13. The dispensing from a multi-channel pipette into the receptacles 13 can be carried out while the holder device 10 is either at a location outside of the transport device 1 or installed in the transport device 1 in a starting position, i.e., before the first of the receptacles 13 is placed on the load receiver 38. As the spacing of the tips of the multi-channel pipette matches the spacing of the receptacles 13 in the holder device 10, all channels of a multi-channel pipette can be emptied into the receptacles 13 simultaneously. This eliminates the time-consuming operation specified in the above-mentioned draft standards of individually dispensing liquid from each channel and the associated n-fold repetition of aspirating (taking in) and ejecting liquid with a pipette that has n channels. It has proven practical to put an additional receptacle 13 ahead of and behind the series of filled receptacles in the holder device 10 for the purpose of determining the rate of evaporation.

The calibration process with the apparatus of the foregoing description is carried out, for example, as follows:

First, the transport device 1 runs the empty receptacles 13 through a tare-weighing process to determine the empty receptacle weights and store them, e.g., in a memory unit of the electronic balance. A defined quantity of test liquid is put into the first and last of the receptacles 13, e.g., from an already calibrated pipette, for the determination of the evaporation rate. Subsequently, the test liquid is aspirated into all channels of the pipette and then dispensed into all of the remaining receptacles 13 simultaneously. At this point of the test, the holder device 10 can be positioned either in the transport device 1 or outside of the latter. Thus, it is possible to dispense liquid into receptacles in advance, i.e., while the calibration apparatus is occupied with a preceding calibration or tare-weighing operation. After the holder device 10 has been set into the transport carriage 8 in the transport device 1, the first receptacle 13, which may be one of the additional receptacles for the measurement of the evaporation rate, is advanced to the balance 37 and weighed. Next, the first of the receptacles 13 into which the multi-channel pipette was emptied is advanced to the load receiver 38 and weighed. The same motion that removes one receptacle 13 from the load receiver, places the next receptacle on the load receiver, where the receptacle is weighed together with the liquid. The cycle is repeated for each of the receptacles into which one of the pipette channels has been discharged. It is an important factor in this process that all of the receptacles 13 are placed on the load receiver 38 in identical manner. As is evident from the foregoing description, the inventive apparatus is very advantageously designed to ensure the precise, repeatable positioning of the receptacles 13 on the load receiver 38. The weighing of the last receptacle 13 serves to determine the evaporation rate. For additional confirmation of the evaporation value, the transport direction is reversed and the carriage is returned directly to the beginning position to weigh the first of the receptacles 13 a second time. The evaporation rate is determined, e.g., by assuming that the weight decrease from evaporation is linear over the time span from the first to the last weighing of a series, and a corresponding evaporation loss is figured into the volume calculation for each channel of the pipette. The weighing cycle periods for the receptacles should be of uniform length, in view of the settling time constant of the balance 37 and also to keep the process consistent with the assumption that the weight loss from evaporation is a linear function of the time. In addition, environmental parameters, specifically temperature, barometric pressure and humidity have to be measured continuously, as well as the temperature of the test liquid. The atmospheric pressure and especially the temperature of the test liquid are entered into the calculation of the test volume based on the weight and density of the test fluid. The other environmental parameters are monitored to check and maintain constant test conditions, which are important particularly in view of the evaporation of the test liquid.

The calibration test according to the foregoing description as well as variations thereof may be stored as computer program routines in a memory unit of the electronic balance.

Figure 10:
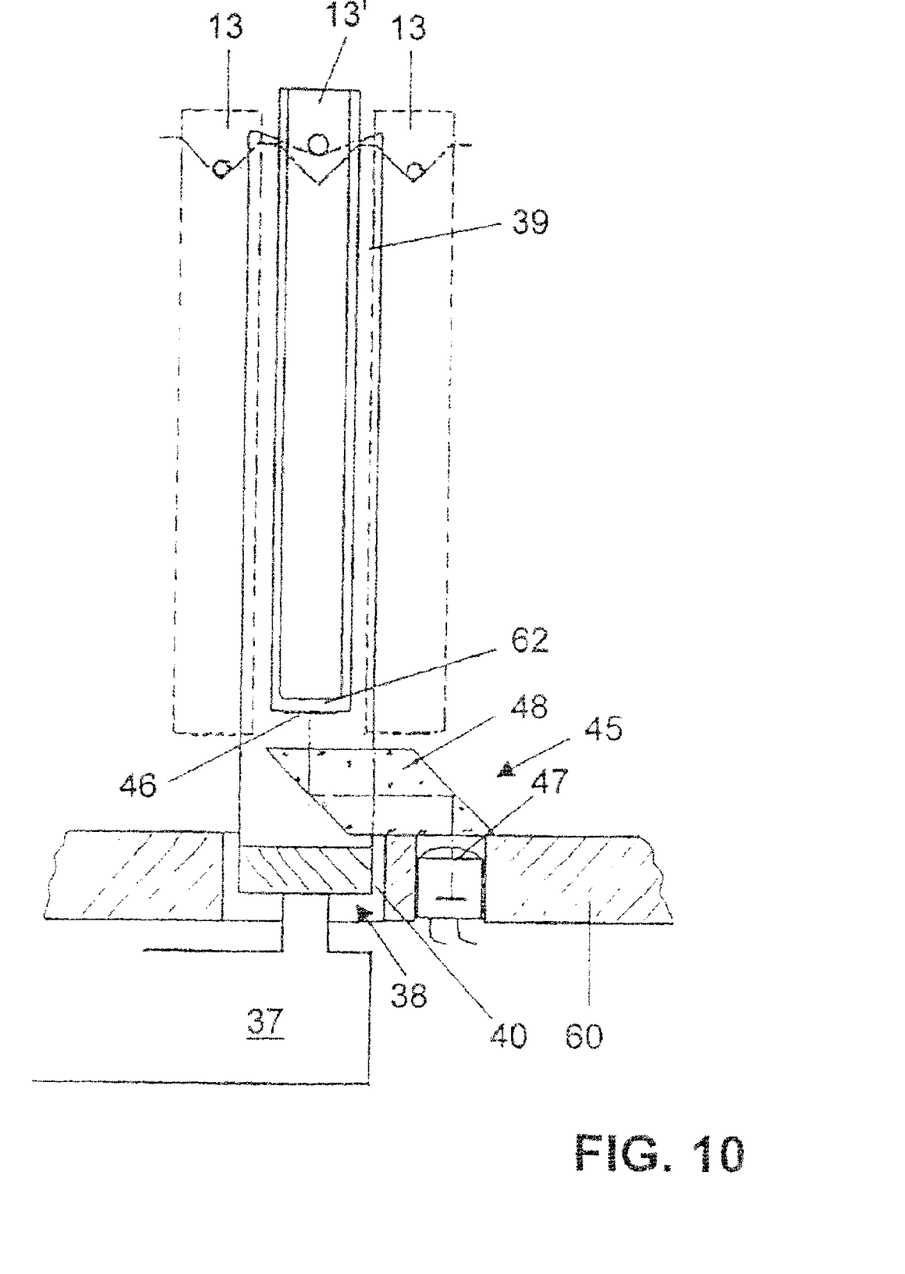
FIG. 10 represents an exemplary integrated code reader arrangement near the load receiver, with code markings attached to the bottoms of the receptacles.

FIG. 10 illustrates a receptacle 13' resting on the load receiver 38 in a slightly raised position in relation to the preceding and following receptacles 13. Also shown in FIG. 10 is a code reader arrangement 45, which is installed in the lower portion of the housing 2 and serves to receive data concerning the test fluid and/or the receptacles 13, 13'. For example, an arrangement for reading an optical code 46 on the bottom surface 62 of the receptacle may have a sensor head 47 with a laser diode and a photo diode. The laser diode emits light which, after reflection on the coded marking 46, is received by the photo diode. The code may be a bar code or a matrix code. To avoid placing the sensor head 47 directly on the load receiver 38, the code reader arrangement 45 includes elements to redirect the light on its way from the sensor head 47 to the receptacle bottom 62 and back to the sensor head. In the illustrated example of FIG. 10, the light path is defined by means of a rhomboid prism 48 that extends into the space between the wings 39 of the load receiver 38. Of course, it is also possible to install other optical elements to direct the light, depending on the geometry of the arrangement. Furthermore, the code reader arrangement 45 is not restricted to optical devices. It is also conceivable to use a system based on a magnetic principle or on radio waves. Nevertheless, if the balance 37 contains a weighing cell based on electromagnetic force compensation, an optical principle is preferred for the code reader device 45.

Figure 11:
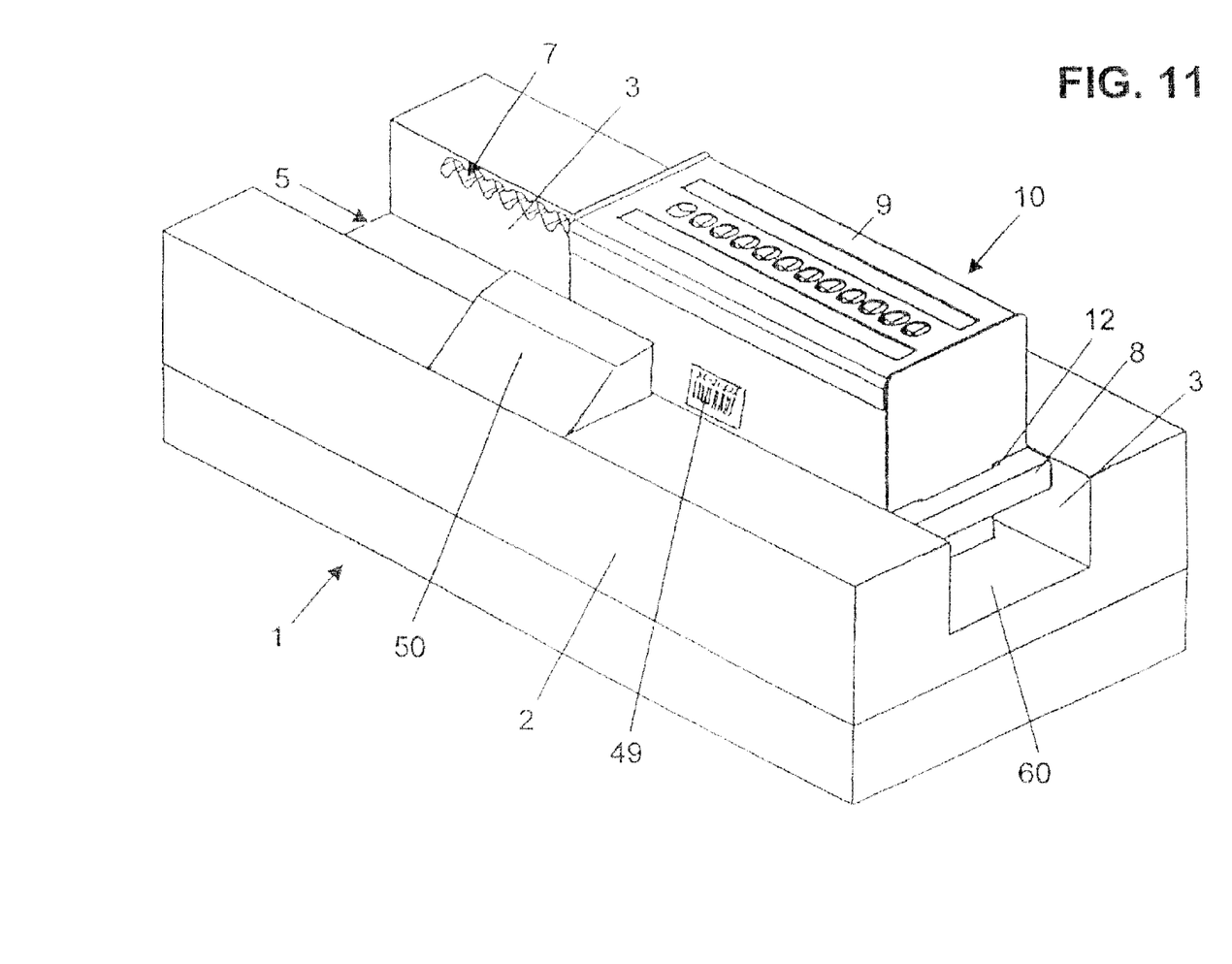
FIG. 11 represents a perspective view of an exemplary transport device with a bar code marking on the holder device and a bar code reader mounted on the transport device.

However, the concept of using a coded identification does not have to be limited to the receptacles 13. It may also be useful to mark the holder device 10 with a code, e.g., a bar code 49 or a matrix code, and to read the code with a scanner 50, as shown in FIG. 11. The bar code 49 is arranged laterally on the holder device 10, with the scanner 50 arranged at the same height in a top-mounted attachment to the transport device 1.

Marking individual receptacles or an entire holder device 10 by means of a code is useful in particular if the transport device 1 is employed not only for calibrating multi-channel pipettes but for any laboratory applications that require samples to be transported to a measuring apparatus. Marking of an individual holder device 10 is necessary, if the holder device is separable from the transport device and if more than one holder device is used, for example in a procedure where one holder device is being loaded with samples while the transport device 1 runs the other holder device through the measurement process.

The inventive concept can also be applied to transport devices that move the holder device along a closed-loop track, e.g., a circle. It is also conceivable to use a circular design for the holder device 10 itself, which is a particularly useful configuration if a large number of receptacles are to be transported to a measuring device.

LIST OF REFERENCE SYMBOLS

| | |
|---|---|
| 1 | transport device |
| 2 | housing |
| 3 | side wall |
| 4 | bottom side |
| 5 | transport channel |
| 6 | arched upper profile |
| 7 | transport rack |
| 8 | transport carriage |
| 9 | cover |
| 10 | holder device |
| 11 | foot portion |
| 12 | seat for holder device |
| 13, 13' | receptacle |
| 14 | side wall |
| 15 | tub |
| 16 | holder rack |
| 17 | tips |
| 18 | indentation |
| 19, 19' | suspension members |
| 20 | fill openings |
| 21 | transparent window |
| 22 | retainer rack |
| 23 | socket |
| 24, 24' | rod member |
| 25 | inner cone |
| 26 | outer cone |
| 27 | double cone |
| 28 | ring groove |
| 29 | receptacle of circular cross-section |
| 30 | receptacle of oval cross-section |
| 31 | receptacle of oblong rectangular cross-section |
| 32 | receptacle of compact rectangular cross-section |
| 33 | pin |
| 34 | lateral guide peg |
| 35 | drive mechanism |
| 36 | drive rack |
| 37 | balance |
| 38 | load receiver |
| 39 | lateral wing |
| 40 | opening |
| 41 | V-shaped depression |
| 42 | arch |

-continued

| | |
|---|---|
| 43 | tooth |
| 44 | pipette tip |
| 45 | code reader device |
| 46 | optical code |
| 47 | sensor head |
| 48 | rhomboid prism |
| 49 | bar code |
| 50 | scanner |
| 51 | drive wheel |
| 52 | bolt or roller |
| 53, 53' | suspension members |
| 54 | trapeze-shaped indentation |
| 55 | trapeze-shaped indentation |
| 56 | trapeze-shaped indentation |
| 57 | shaft |
| 58 | pressure sensor |
| 59 | base of load receiver |
| 60 | floor of the transport channel |
| 61 | arches of the drive rack |
| 62 | receptacle bottom |

What is claimed is:

1. An apparatus for gravimetrically calibrating a multi-channel pipette, comprising:
a balance with a load receiver configured to support one of a plurality of receptacles;
a holder device configured to hold the plurality of receptacles, said receptacles being seated in the holder device at defined equal intervals from each other and arranged so that the receptacles can be filled with a test liquid from pipette tips of the multi-channel pipette; and
a transport device for transporting the holder device to the load receiver, wherein the transport device has means for placing on and subsequently removing from the load receiver one after another of said receptacles.

2. The apparatus of claim 1, wherein at least one of the transport device and the holder device has means for precisely positioning the receptacles on the load receiver.

3. The apparatus of claim 1, wherein the transport device is encased in a housing, the balance is installed in the housing, and the load receiver is arranged on a surface of the balance and passes through an opening of the housing into the holder device, when the holder device is in a working position on the transport device.

4. The apparatus of claim 1, wherein the load receiver has two wings with V-shaped depressions formed at ends of the wings, from which said one of the plurality of receptacles can be suspended.

5. The apparatus of claim 1, wherein the defined equal intervals correspond to a tip interval at which the pipette tips of the multi-channel pipette are spaced from each other.

6. The apparatus of claim 1, wherein the plurality of receptacles in the holder device has at least as many receptacles as the multi-channel pipette has pipette tips.

7. The apparatus of claim 1, wherein the receptacles have a geometrically shaped cross-section selected from the group consisting of a circle, oval and rectangle.

8. The apparatus of claim 1, wherein the holder device comprises:
a holder rack with indentations in which the receptacles are seated by means of rigid suspension members that are attached to upper ends of the receptacles.

9. The apparatus of claim 8, wherein the rigid suspension members comprise:
sockets that partially surround a circumference of each receptacle, and rod members with an inner cone and an outer cone.

10. The apparatus of claim 9, wherein at least one of the rod members has a double cone which includes two cones pointing in opposite directions, located between the inner cone and the outer cone, and forming a ring groove at a transition from the double cone to the outer cone, said ring groove serving to positively seat one of the rigid suspension members in one of the indentations of the holder rack.

11. The apparatus of claim 1, wherein the holder device is separable from the transport device.

12. The apparatus of claim 1, wherein the holder device has a cover as a barrier against contamination and evaporation.

13. The apparatus of claim 1, wherein the holder device has at least one tub near openings of the receptacles, wherein the tub can be filled with the test liquid to create a saturated atmosphere in the holder device to reduce evaporation of the test liquid from the receptacles.

14. The apparatus of claim 1, wherein the holder device has means whereby an underside of the holder device is sealed when the holder device is set on a flat surface.

15. The apparatus of claim 1, wherein the transport device is operable to move the holder device horizontally back and forth while at the same time raising and lowering the holder device.

16. The apparatus of claim 15, wherein the transport device is configured to move the holder device back and forth with simultaneous raising and lowering with a single drive source.

17. The apparatus of claim 16, wherein the single drive source is an electric motor.

18. The apparatus of claim 16, comprising:
a drive mechanism, a housing, a drive wheel with at least two bolts, and a drive rack with arcuate cutouts, wherein the drive mechanism and the drive wheel are attached to the housing, the drive rack is attached to one of a transport carriage of the transport device and the holder device, and the bolts are configured to engage the arcuate cutouts of the drive rack.

19. The apparatus of claim 18, wherein the drive rack, the transport rack of the transport device, and a holder rack of the holder device are shaped with a common periodic pitch.

20. The apparatus of claim 1, wherein the transport device has a transport carriage and a transport channel in which the transport carriage moves, and wherein the transport carriage has a seat for the holder device.

21. The apparatus of claim 1, wherein the transport device comprises:
at least one transport rack guiding movements of the holder device.

22. The apparatus of claim 1, wherein the transport device comprises:
a position sensor operable to determine an actual position of one of the holder device and a transport carriage of the transport device in relation to the transport device.

23. The apparatus of claim 1, wherein the holder device is guided by the transport device along a linear travel path.

24. The apparatus of claim 1, wherein the holder device is guided by the transport device along a circular travel path.

25. The apparatus of claim 1, wherein each receptacle has a bottom surface marked with a receptacle code, and the transport device has a sensor head, and wherein signal-conducting means are provided for transmitting a code signal from the receptacle code to the sensor head.

26. The apparatus of claim 1, wherein the holder device is marked with a holder device code and the transport device comprises:
a sensor device that is operable to read the holder device code and is arranged at an even level with the holder device code.

* * * * *